United States Patent [19]

Young

[11] Patent Number: 4,587,488

[45] Date of Patent: May 6, 1986

[54] NUCLEAR MAGNETIC RESONANCE METHODS AND APPARATUS

[75] Inventor: Ian R. Young, Middlesex, England

[73] Assignee: Picker International, Limited, Wembley, England

[21] Appl. No.: 519,832

[22] Filed: Aug. 3, 1983

[30] Foreign Application Priority Data

Aug. 19, 1982 [GB] United Kingdom ............... 8223862

[51] Int. Cl.$^4$ ........................................... G01R 33/20
[52] U.S. Cl. ..................................... 324/306; 324/309
[58] Field of Search ................ 324/300, 306, 309, 314

[56] References Cited

U.S. PATENT DOCUMENTS

| | | | |
|---|---|---|---|
| 4,458,203 | 7/1984 | Young | 324/309 |
| 4,516,075 | 5/1985 | Moran | 324/309 |
| 4,516,582 | 5/1985 | Redington | 324/309 |
| 4,520,828 | 6/1985 | Burl | 324/309 |
| 4,523,596 | 6/1985 | Macovski | 324/309 |

OTHER PUBLICATIONS

Singer, "NMR Flow Imaging", Proceedings of an International Symposium on NMR Imaging, Oct. 1–3, 1981.

*Primary Examiner*—Michael J. Tokar
*Attorney, Agent, or Firm*—Watts, Hoffmann, Fisher & Heinke Co.

[57] ABSTRACT

A method and apparatus for determining the rate of flow of a liquid in a region of a body using a nuclear magnetic resonance technique. Nuclear magnetic resonance is excited firstly preferentially in a slice of the body which includes the region and then over the whole of the body. A period of time is allowed to elapse, and nuclear magnetic resonance is then excited preferentially in the slice. The free induction decay signal is then measured, and the signal is related to the state of flow of the liquid through the slice.

8 Claims, 3 Drawing Figures 4,587,488

NUCLEAR MAGNETIC RESONANCE METHODS AND APPARATUS

TECHNICAL FIELD

This invention relates to methods and apparatus for determining the rate of flow of a liquid in a selected region of a body by nuclear magnetic resonance (NMR) techniques. It has particular relevance to techniques for measuring relatively low rate of flow.

BACKGROUND ART

NMR techniques have been used for the chemical analysis of material for many years. More recently NMR techniques have been used to obtain images representing the distribution over a selected cross-sectional slice or volume of a body of a chosen quantity, e.g. the density of chosen nuclei, for example hydrogen protons, or of NMR spin relaxation time constants. Such distributions are similar to, although of different significance from, the distribution of X-ray attenuation provided by computerised tomography systems.

DISCLOSURE OF THE INVENTION

In some applications it would be useful to obtain additional information relating to the flow rates of a liquid within a selected region of the body, e.g. blood flow in selected veins and arteries of a human body, using NMR techniques.

It is an object of the invention to provide a method of determining the rate of flow of a liquid in a selected region of a body by NMR techniques.

According to the present invention a method of determining the rate of flow of a liquid in a region of a body comprises: exciting nuclear magnetic resonance preferentially in a slice of said body which includes said region; subsequently exciting nuclear magnetic resonance substantially over the whole of said body; waiting a period of time and then again exciting nuclear magnetic resonance preferentially in said slice; measuring the resultant free induction decay signal; and relating said signal to the rate of flow of said liquid through said slice.

Preferably during said period of time there are applied magnetic fields effective to cause dephasing of the nuclear magnetic resonance except in said slice.

The invention also provides an apparatus arranged to determine the rate of flow of a liquid in a region of a body, comprising: means arranged to excite nuclear magnetic resonance preferentially in a slice of said body which includes said region; means arranged to subsequently excite nuclear magnetic resonance substantially over the whole of said body; means arranged to wait a period of time and then again excite nuclear magnetic resonance preferentially in said slice; means arranged to measure the resultant free induction decay signal; and means arranged to relate said signal to the rate of flow of said liquid through said slice.

BRIEF DESCRIPTION OF THE DRAWINGS

One method and apparatus in accordance with the invention will now be described, by way of example only with reference to the accompanying drawings in which.

BEST MODE FOR CARRYING OUT THE INVENTION

The method is performed using an apparatus essentially identical to that described in U.K. Patent Specification No. 1,578,910 or No. 2,056,078 to which reference should be made for a fuller description, appropriately programmed to apply a sequence of magnetic field gradient and RF pulses and analyse the resulting signals as hereafter described.

The essential features of such an apparatus in so far as is required for an understanding of the present invention are as follows:

The apparatus includes a first coil system whereby a magnetic field can be applied to a body to be examined in a given direction, normally designated the Z-direction, with a gradient in any one or more of the three orthogonal directions i.e. X, Y and Z directions.

Figure 1:
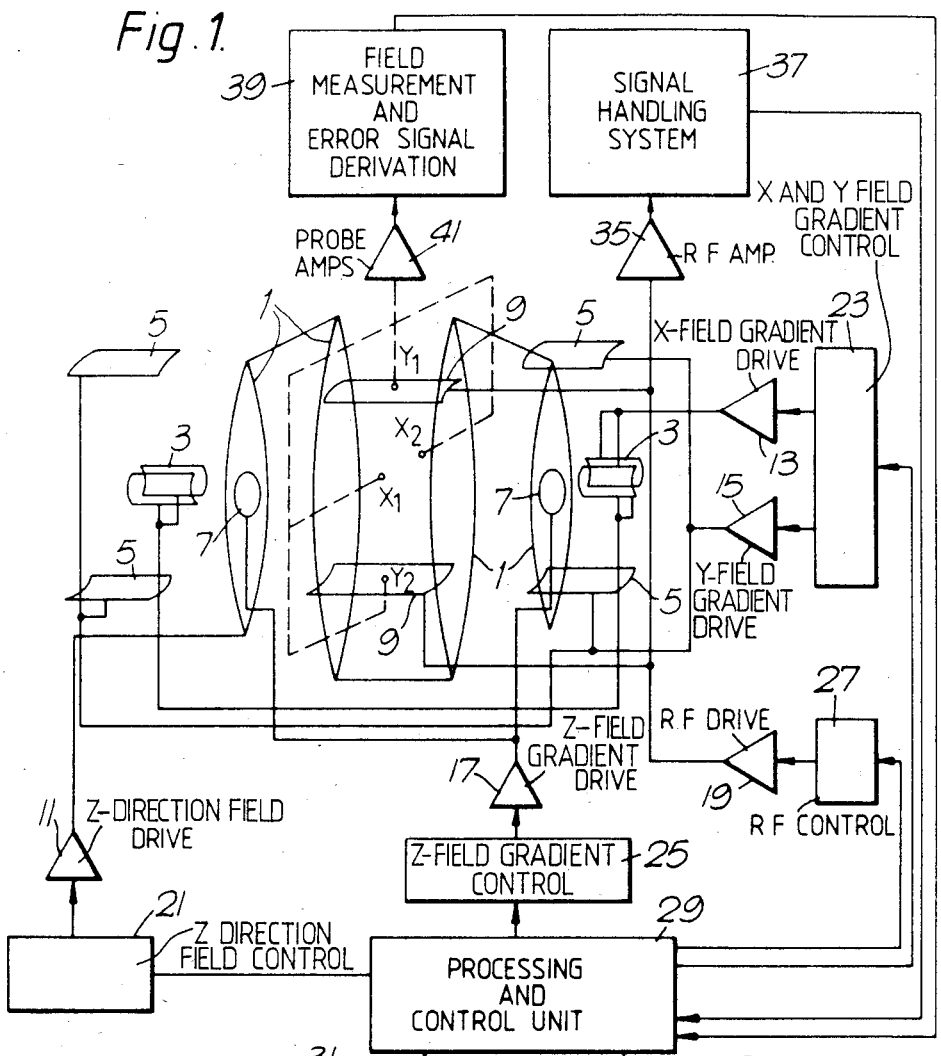
FIGS. 1 and 2 illustrate the apparatus diagrammatically.

Referring to FIG. 1, the first coil system comprises coils 1 capable of providing a steady uniform magnetic field in the Z direction; coils 3 capable of providing a magnetic field gradient in the X direction, coils 5 capable of providing a magnetic field gradient in the Y direction; and coils 7 capable of providing a magnetic field gradient in the Z direction.

In addition, the apparatus includes a second coil system 9 whereby RF magnetic fields can be applied to the body under examination in a plane normal to the direction of the steady uniform magnetic field produced by the first coil system, and whereby RF magnetic fields resulting from nuclei in the body under examination which have been excited to nuclear magnetic resonance with a spin vector component other than in the Z direction can be detected.

In the drawing a single pair of coils 9 is shown for both applying and detecting RF fields, but in certain circumstances it may be preferable to provide separate coils for detecting the RF fields.

The various coils 1, 3, 5, 7 and 9 are driven by drive amplifiers 11, 12, 13, 15, 17 and 19 respectively, controlled by control circuits 21, 23, 25 and 27 respectively. These circuits may take various forms which are well known to those with experience of NMR equipment and other apparatus using coil induced magnetic fields.

The circuits 21, 23, 25 and 27 are controlled by a central processing and control unit 29 with which are associated inputs and other peripherals 31, for the provision of commands and instructions to the apparatus, and a display 33.

The NMR signals detected by the coils 9 are applied via an amplifier 35 to a signal handling system 37. The signal handling system is arranged to make any appropriate calibration and correction of the signals, but essentially transmits the signals to the processing and control unit 29 wherein the signals are processed for application to the display to produce an image representing the distribution of an NMR quantity in the body being examined.

It will be appreciated that whilst shown separately to clarify the present description, the signal handling system 37 may conveniently form part of the unit 29.

Figure 2:
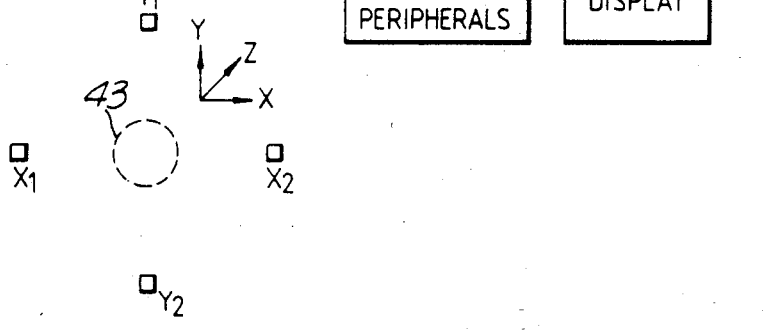

The apparatus also includes field measurement and error signal circuits 39 which receive signals via amplifiers 41 from field probes $X_1$, $X_2$, $Y_1$ and $Y_2$ which are disposed at suitable positions in relation to a slice 43 of the body being examined, as illustrated in FIG. 2, to monitor the applied magnetic fields.

Figure 3:
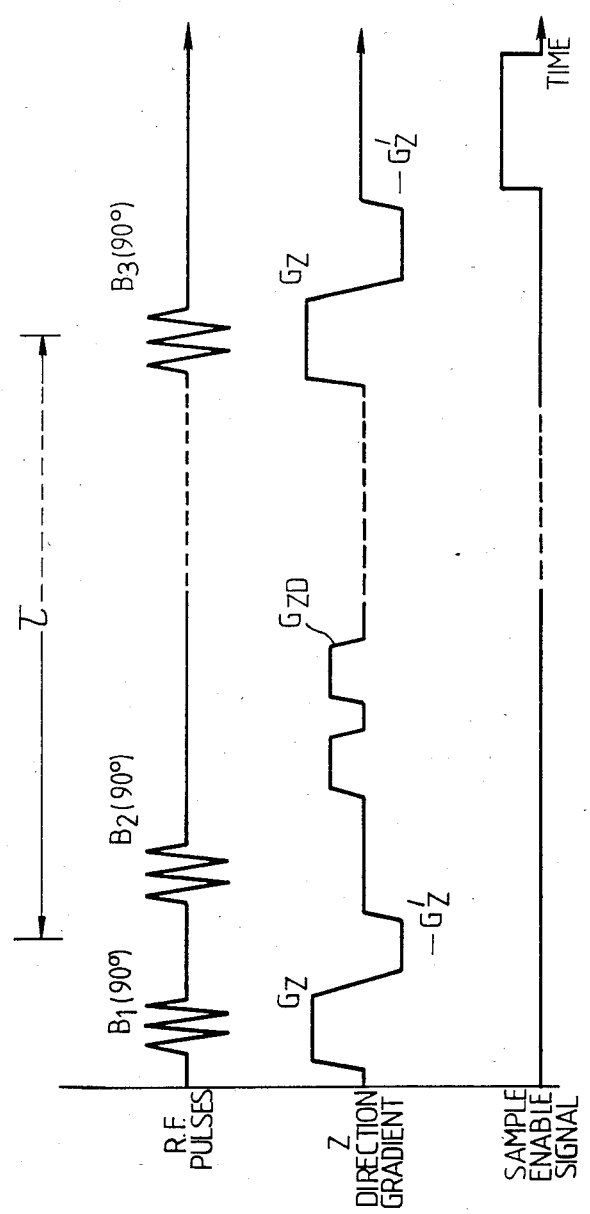
FIG. 3 illustrates the magnetic field sequence employed in the method.

Referring now also to FIG. 3, in operation of the apparatus a steady uniform magnetic field Bo is applied to the body under examination in the Z direction. This field serves to define the equilibrium axis of magnetic alignment of the nuclei in the body i.e. along the Z direction, and remains constant throughout the examination procedure. A magnetic field gradient Gz along the Z direction is then applied to the body, together with an RF magnetic field pulse denoted $B_1$ (90°), for reasons explained hereafter. The frequency of the RF field is chosen to be the Larmor frequency for protons in a slice 43 of the body, normal to the Z direction, the slice being defined by a particular magnetic field along the Z direction, such that protons within the slice are preferentially excited, the slice consisting of an area of substantially solid material through which a series of blood vessels extend. The integral of the RF pulse is such that the pulse is just sufficient to tip the spins of the excited protons into the X-Y plane, and is thus referred to as a 90° pulse, the spins then precessing in the X-Y plane round the Z axis.

The field gradient Gz is then removed, and replaced by a gradient in the opposite sense $-Gz'$. This causes the rephasing of the spins which have been selectively excited by the combination of the RF pulse $B_1$ (90°), Bo and the field gradient Gz, the dephasing having been caused by the gradient through the slice. The magnitude of $-Gz'$ is adjusted so that the spins are rephased at the time at which this gradient is switched off as described, for example, in the above mentioned UK Patent Specification No. 1,578,910. Immediately after the $-Gz'$ pulse, a second RF magnetic field pulse $B_2$(90°) having the same characteristics as the $B_1$(90°) pulse is applied. As it is applied in the absence of any magnetic field gradients it is effective to excite the spins of all the hydrogen protons within the body. Thus the spins within the slice which were already in the X-Y plane are rotated to the $-Z$ direction, whilst the excited spins in the rest of the body are tipped into the X-Y plane.

A period of time, $\tau$, is then allowed to elapse, during which time the excited spins throughout the body relax back towards the positive Z direction. During this period a number of pulsed magnetic field gradients Gzd may be imposed along the Z direction, these pulses causing phase dispersion of spins lying in the X-Y plane in addition to the phase dispersion of the spins which naturally occurs, due to spin-spin interaction ($T_2$ effects). The gradients Gzd do not however affect spins in the Z directions. Thus these pulses reduce the signal which would be induced in the second coil system by spins outside the selected slice which have remained in the X-Y plane although for long values of $\tau$ this signal would in any case be small.

After the time period $\tau$ has elapsed, a third RF magnetic field pulse $B_3$(90°) again having the same characteristics as the $B_1$(90°) pulse is applied in the presence of the magnetic field gradient to selectively excite the protons within the slice as before, this sequence again being followed by the rephasing gradient $-Gz'$. The signal induced in the second coil signal by these spins, i.e. the Free Induction Decay (F.I.D.) system 9 is then recorded, the spins outside the slice which remain in the XY plane after the period having been dephased as explained hereinbefore, and thus not contributing significantly to the measured signal.

The magnitude of the measured F.I.D. signal is related to the density of protons within the slice, and will consist of contributions from hydrogen protons in three different circumstances:

(1) protons in the solid material in the slice;

(2) protons in the blood which has remained in the slice during the period from the $B_1$(90°) and $B_2$(90°) pulses to the recording of the F.I.D. signal, i.e. a period substantially equal to $\tau$; and (3) hydrogen protons in the 'new' blood which has flowed into the slice during the period.

Dealing firstly with the protons from the solid material in the slice, a proportion $\rho_{OS}e^{-\tau/T_1S}$ of the spins of the total density $\rho_{OS}$ of the hydrogen protons in the solid material will, after the period $\tau$, have remained aligned along the $-Z$ direction, where $T_{1S}$ is the spin-lattice relaxation time for hydrogen protons within the solid material. The remainder of the spins, $\rho_{OS}$ $(1-e^{-\tau/T_1S})$ will have relaxed back into their equilibrium alignment along the positive Z direction. After the $B_3$ (90°) pulse, as the spins originating from the positive and negative Z directions respectively are 180° out of phase within the X-Y plane, the net contribution to the measured signal will be $\tau_{OS}(1-2e^{-\tau/T_1S})$. As in practice the whole pulse sequence is repeated several times, there will be a further contribution to the signal originating from the hydrogen protons in the solid material in the slice of the form $\tau_{OS}e^{-t_d/T_1S}$, where $t_d$ is the time which has passed between the $B_1$ (90°) pulses in each pair of sequences, to compensate for the spins not being in their equilibrium condition i.e. aligned along the positive Z direction, at the beginning of each pulse sequence. Thus the total contribution $\tau_1$ to the measured F.I.D. signal from the solid material in the slice will be of the form:

$$\rho_1 = \rho_{OS}(1 - 2e^{e_1S} + e^{-t_d/T_1S})$$

i.e. the usual form of expression for inversion recovery experiments.

Dealing now with the contribution of hydrogen protons in the blood which has remained in the slice during the period $\tau$, a proportion $\rho_{OB}\,Av\tau$ of the blood in the slice will have flowed out of the slice during this period, where $\rho_{OB}$ is the hydrogen proton density for blood in the slice;

A is the cross sectional area of the blood vessels through the slice; and v is the velocity of the blood through the vessels.

This, therefore, leaves a proportion $\rho_{OB}(1-Av\tau)$ of the blood remaining in the slice. An expression $\rho_2$ for the contribution to the measured signal from the blood remaining in the slice can therefore be written:

$$\rho_2 = \rho_{OB}(1-Av\tau)(1-2e^{-\tau/T_1B}+e^{-t_d/T_1B})$$

where $T_{1B}$ is the spin-lattice relaxation time for blood in the vessels within the slice.

Finally, considering the 'new' blood which has flowed into the slice during the time period $\tau$ to replace the blood which has flowed out, all the spins which contribute to the measured F.I.D. signal within this blood will have been aligned along the positive Z direction prior to the $B_3$(90°) pulse, and thus the contribution $\tau_3$ from these spins will be of the form:

$$\rho_3 = \rho_{OB}Av(1-e^{-\tau/T_1B})$$

Thus the total F.I.D. signal measured will be related to the sum $\tau_1+\tau_2+\tau_3$. As $T_{1S}$ and $T_{1B}$ can be estimated, and $\tau$ and $t_d$ are known, after a series of pulse sequences with different values of $\tau$, the velocity v of the blood through the vessels in the slice can be calculated. If however $\rho_{OS}$, $\rho_{OB}$ and A can be estimated it will, of course only be necessary to perform the pulse sequence once although it might be advantageous to average the signal over several measurements to improve the signal to noise ratio.

It will be appreciated that the choice of the time $\tau$ is determined by the values of the spin-lattice relaxation times $T_{1S}$ and $T_{1B}$. As these times can for many tissues be relatively long, in the order of 400 m.secs, relatively slow flow rates can readily be monitored by this method. Due to the long time periods available the magnitude of the applied gradients can be minimised, and thus the resonance signal from excited spins within the body are dispersed relatively slowly. The F.I.D. signal will then persist above noise levels for longer, and also sharp resonance lines will be maintained. This is particularly advantageous where it is desired to also measure the chemical shift in the Larmor frequency between for example, protons in the blood and protons in the solid material in the slice.

It will also be appreciated that whilst the method described hereinbefore relates to determining the rate of flow of a liquid which contains protons, the method is equally applicable to determining the rate of flow of a liquid containing other nuclei having a magnetic spin, e.g. $^{31}P$, by appropriate choice of the RF pulse frequency.

I claim:

1. A method of determining the rate of flow of a liquid in a region of a body comprising: first exciting nuclear magnetic resonance selectively in a slice of said body which includes said region; subsequently exciting nuclear magnetic resonance substantially over the whole of said body; waiting a period of time and then again exciting nuclear magnetic resonance selectively in said slice the time between said first exciting and said again exciting being less than the spin lattice relaxation time for the nuclei excited during said excitations; measuring the subsequent free induction decay signal; and relating said signal to the rate of flow of said liquid through said region.

2. A method according to claim 1 in which during said period of time there are applied magnetic fields effective to cause dephasing of the nuclear magnetic resonance except in said slice.

3. A method according to claim 1 in which each of said excitations is effective to rotate the spins of a chosen nuclei within said slice through substantially 90°.

4. A method of determining the rate of flow of a liquid in a region of a body comprising performing the sequence of steps comprising the method according to claim 1 several times.

5. A method according to claim 4 wherein the said period of time is different for each said sequence of steps.

6. An apparatus arranged to determine the rate of flow of a liquid in a region of a body comprising: means arranged to first excite nuclear magnetic resonance selectively in a slice of said body which includes said region; means arranged to subsequently excite nuclear magnetic resonance substantially over the whole of said body; means arranged to wait a period of time and then again excite nuclear magnetic resonance selectively in said slice the time between said first exciting and said again exciting being less than the spin lattice relaxation time for the nuclei excited during said excitations; means arranged to measure subsequent free induction decay signal; and means arranged to relate said signal to the rate of flow of said liquid through said region.

7. An apparatus according to claim 6 including means arranged to apply magnetic fields during said period of time which are effective to cause dephasing of the nuclear magnetic resonance except in said slice.

8. An apparatus according to claim 6 in which each of said means arranged to excite is effective to rotate the spins of a chosen nuclei within said slice through substantially 90°.

* * * * *

UNITED STATES PATENT AND TRADEMARK OFFICE
CERTIFICATE OF CORRECTION

PATENT NO. : 4,587,488
DATED : May 6, 1986
INVENTOR(S) : Ian R. Young

It is certified that error appears in the above-identified patent and that said Letters Patent is hereby corrected as shown below:

Column 4, line 24, "$\tau$" should be --$\rho$--;
Column 4, line 28, "$\tau$" should be --$\rho$--;
Column 4, line 33, "$\tau$" should be --$\rho$--;
Column 4, line 38, before IS, first occurrence, insert --$t/\tau$--;
Column 4, line 65, "$\tau$" should be --$\rho$--;
Column 5, line 2, "$\tau_1 + \tau_2 + \tau_3$" should be --$\rho_1 + \rho_2 + \rho_3$--.

Signed and Sealed this

Nineteenth Day of August 1986

[SEAL]

Attest:

DONALD J. QUIGG

Attesting Officer

Commissioner of Patents and Trademarks